United States Patent [19]

Bulbenko et al.

[11] 4,045,290
[45] Aug. 30, 1977

[54] DIAGNOSTIC METHOD AND COMPOUNDS FOR USE THEREWITH

[75] Inventors: George F. Bulbenko, Langhorne, Pa.; Joseph Eliot Woodbridge, Princeton, N.J.

[73] Assignee: Princeton Biomedix Incorporated, Princeton, N.J.

[21] Appl. No.: 659,002

[22] Filed: Feb. 18, 1976

Related U.S. Application Data

[63] Continuation-in-part of Ser. No. 554,007, Feb. 28, 1975, abandoned.

[51] Int. Cl.² ............ G07F 3/02; C09K 15/26
[52] U.S. Cl. ............ 195/99; 195/103.5 R; 260/327 S; 252/408; 23/230 B
[58] Field of Search ............ 260/327 S; 252/408 R; 195/103.5 R; 23/230 B

[56] References Cited

U.S. PATENT DOCUMENTS

| | | | |
|---|---|---|---|
| 2,999,793 | 9/1961 | Babson | 195/103.5 |
| 3,331,857 | 7/1967 | Coleman | 260/343.4 |
| 3,689,364 | 9/1972 | Härtel et al. | 195/103.5 |
| 3,823,071 | 7/1974 | Roy et al. | 195/103.5 |
| 3,975,405 | 8/1976 | Hamill | 260/343.4 |

OTHER PUBLICATIONS

Fujimura, C. A. 63:10240a (1965).
Gutmann et al., C. A. 60:8606a (1964).

*Primary Examiner*—Cecilia M. S. Jaisle
*Attorney, Agent, or Firm*—Cantor and Singer

[57] ABSTRACT

An assay for phosphatase enzymes in body fluids comprising contacting a sample of such body fluid with the substrate, Thymol Blue Monophosphate, which is chromogenic at the pH of the reaction mixture and determining activity of the enzyme by measuring the rate of formation of the Thymol Blue dye.

9 Claims, No Drawings

DIAGNOSTIC METHOD AND COMPOUNDS FOR USE THEREWITH

HISTORY OF THE INVENTION

This application is a continuation in part of the U.S. patent application Ser. No. 554,007 filed Feb. 28, 1975 now abandoned.

The subject invention is directed toward a kinetic or end-point assay to determine the amount of active enzyme material present in a test sample. In particular, the subject invention is directed toward the detection of phosphatase enzymes in a sample under improved conditions which allows for both the qualitative and quantitative analysis thereof.

The use of chromogens in connection with enzymatic assays is well documented in the art. In general, a detectable dye or compound having a color of measureable intensity is generated by an enzyme specifically reactive with the chromogenic substrate and the activity of said enzyme is then determined by analysis of the reaction product.

Exemplary of such reactions is the reaction of p-nitrophenol monophosphate under hydrolytic conditions so as to cleave the phosphate linkage and generate p-nitrophenolate ion which absorbs at a wavelength of 405 nm. The amount of said ion is determined spectrophotometrically by measuring the change in optical density at 405nm.

In connection with the p-nitrophenolate ion illustration above, it is noted that such a reaction has been used in the determination of alkaline phosphatase by employing p-nitrophenol monophosphate as a substrate at an alkaline pH (9–10.5) with serum or body fluids containing alkaline phosphatase. There are, however, numerous disadvantages to such an assay, including potential interference by bilirubin and hemoglobin which may be present in the sample of serum to be tested. Both bilirubin and hemoglobin may interfere with the p-nitrophenyl phosphate assay because they absorb in the same region of the spectrum as does the p-nitrophenolate ion and compensation thereof leads to a degree of inaccuracy.

The determination of alkaline phosphatase activity in human sera and the isoenzymes associated therewith is significant because of the known finding that elevated levels thereof are associated with hepatic and bone metabolism disorders such as hepatic disease, biliary tract disease, rickets, osteosarcomas, hyperthyroidism and the like. As a result, several assay procedures for alkaline phosphatase enzyme have been developed over the years. Included among such tests are procedures for the cleavage of $\beta$ - glycerophosphate to glycerol. A test employing thymolphthalein monophosphate as a substrate has also been utilized for the assay of serum phosphatase. As measurement in this test is made at a wavelength of 595 nm, there is minimal interference by bilirubin and hemoglobin.

Thymolphthalein Monophosphate, however, cannot be used as substrate in a kinetic assay procedure since thymolphthalein develops its characteristic color at a pH above the optimum for alkaline phosphatase activity. As a result, the reaction has to be stopped by adding alkali before the color can be read. An accurate, true kinetic assay for determining the level of alkaline phosphatase enzyme in serum, therefore, has utility as a diagnostic tool.

DETAILED DESCRIPTION OF THE INVENTION

Therefore, it is an object of the subject invention to provide a diagnostic test.

Another object of the subject invention is to provide a diagnostic test which is kinetic.

A further object of the subject invention is to provide a diagnostic test in which a detectable dye is released from a chromogenic substrate by reaction with the enzyme to be assayed at a controlled measurable rate without interference from other compounds which may be present.

A still further object of the subject invention is to provide a test for phosphatase enzymes utilizing Thymol Blue Monophosphate as a chromogenic substrate.

As previously noted, there are drawbacks to the measurement of serum phosphatase activity at a wavelength of 405 nm, namely, potential interference of bilirubin and hemoglobin. Other tests wherein measurements are taken at other wavelengths of the spectrum require addition of alkali or other reagents to develop the color to be read. Those procedures, therefore, are not kinetic assays.

The subject invention which eliminates the foregoing difficulties is particularly directed to derivatives of Thymol Blue, particularly Thymol Blue Monophosphate.

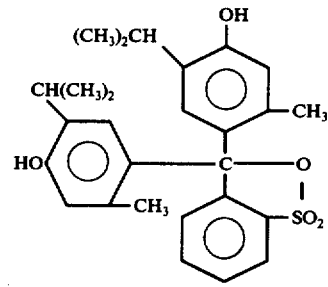

Thymol Blue

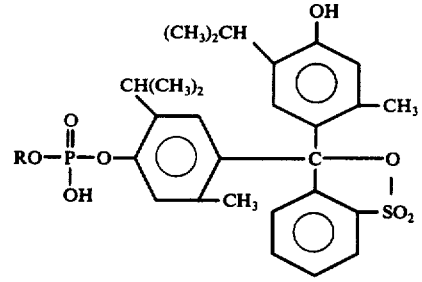

Thymol Blue Monophosphate

R represents Sodium, Potassium, Ammonium, 2-Amino-2-methyl-1, 3-Propanediol, Dicyclohexylamine, Cyclohexylamine, Tris(hydroxymethyl)aminomethane and the like.

The chromophore generated by Thymol Blue Monophosphate absorbs in the 600 nm wavelength region and is detectable immediately under the reaction conditions employed. The reaction, therefore, is a truly kinetic one which is free from interference by elevated levels of bilirubin, hemoglobin and chylomicrons which may be present. Moreover, the sulfonate function of the substrate increases water solubility and avoids interference by metal cations which have created difficulties in other procedures.

Thymol Blue Monophosphate can be readily obtained by reaction of Thymol Blue with POCl₃ followed by hydrolysis to Thymol Blue Phosphoric Acid and neutralization with an inorganic or organic base to form a salt.

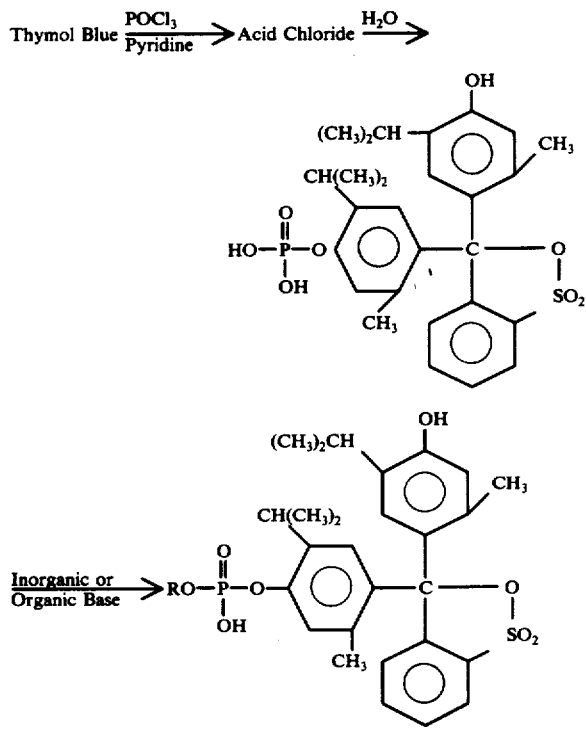

Thymol Blue Monophosphate disclosed herein is affected by alkaline phosphatase at approximately pH 10.2 to produce a strong chromophore at 600 nm, i.e. Thymol Blue, which is measurable continuously and kinetically in any rate reaction spectrophotometer equipped to operate at that wavelength. On the other hand, Thymol Blue Monophosphate, when used for detecting acid phosphatase at pH 4-5.5, will require a quenching with a high pH buffer in order to generate Thymol Blue chromophore for absorbance measurement.

According to the test procedure of the subject invention, Thymol Blue Monophosphate is hydrolyzed by alkaline phosphatase to Thymol Blue in the presence of phosphorylatable diethanolamine buffer at pH 10.2. The color produced as a result thereof is proportional to enzyme present and the average change in absorbance per minute ($\Delta A$/min) is determined at a wavelength of 600 nm. The subject test procedure does not have an induction period and the activity of the enzyme may be determined as soon as a rate has been established. The reaction proceeds as follows:

where
ROH is an amino alcohol or water
ALP is Alkaline Phosphatase

According to the test procedure of the subject invention, a substrate reagent solution is prepared containing Thymol Blue Monophosphate, diethanolamine or other suitable phosphorylatable amino alcohol, or water, metal ion activators such as, for example, magnesium ion and such other additives that do not interfere with the reaction but which may be desirable as stabilizers, surfactants, antimicrobial agents and the like. Other amino alcohol buffers which can be phosphorylated and which can be used in this test are, for example, 2-ethylaminoethanol, 3-dimethylamino-1, 2-propanediol, 2-methylaminoethanol, those listed by Elias Amador, *Clinical Chemistry*, 18, 94 (1972) and the like. The amino alcohol buffer is present in an amount sufficient to raise the pH of the reaction mixture to about 10.2. The magnesium activator is used in an amount sufficient to activate the alkaline phosphatase enzyme in the sample to be tested. The concentration of magnesium ion in the substrate reagent is about 1.5 millimoles per liter. The concentration of Thymol Blue Monophosphate in the reagent is not critical but must be sufficient to permit a kinetic reaction to proceed over a period of time without the substrate being exhausted. The preferred concentration of this material is between 1 and 3 millimoles per liter. The serum sample to be tested is contacted with the substrate reagent at a given temperature which may be from about 22° to about 40° C but preferably at 30° C or 37° C. While the temperature affects the rate of reaction, the particular temperature used, within the limits of the stability of the sample, is not critical hereto. The average change in absorbance per minute ($\Delta A$/min) at 600 nm is then determined in a spectrophotometer capable of reading absorbance at 600 nm and maintaining constant temperature in the cuvet compartment. By definition, one unit of alkaline phosphatase activity is the amount of enzyme that will hydrolyze one micromole of Thymol Blue Monophosphate to Thymol Blue in one minute at 30° C. The enzyme activity is calculated by the following formula:

$$U/\text{liter} = \frac{\Delta A/\text{min} \times 10^6 \times \text{reaction volume} \times Tf}{3.51 \times 10^4 \times \text{volume of sample}}$$

$$= \frac{\Delta A/\text{min} \times 10^6 \times 2.05 \times Tf}{3.51 \times 10^4 \times 0.05}$$

$$= \Delta A/\text{min} \times 1168 \times Tf$$

where:
U/liter = units of enzyme activity per liter at 30° C
$10^6$ = conversion of moles to micromoles
$3.51 \times 10^4$ = molar absorptivity of Thymol Blue at 600 nm
Tf = temperature factor to convert to rate at 30° C
reaction volume = 2.05 ml
sample volume = 0.05 ml
Sample calculation:
$\Delta A$/min at 600 nm = 0.013
Reaction Temperature 30° C, Tf = 1
Sample Volume = 0.05 ml
Reagent Volume = 2.0 ml
U.liter = 0.013 × 1168 × 1 = 15.2

The normal values of alkaline phosphatase activity in adults as found by this test is 5 to 23 U/liter. This range is based on results obtained on 200 clinically normal adults. Children normally have higher serum alkaline phosphatase levels due to active bone growth. The upper levels of normal in children can be twice as high as in adults.

If so desired an end-point procedure may be employed for determination of serum alkaline phosphatase activity employing Thymol Blue Monophosphate as the substrate. In this instance, the test serum sample is added to the diethanolamine buffered Thymol Blue Monophosphate substrate solution and the reaction is terminated after 10 minutes time by addition of an alkaline reagent such as, for example, 0.1M NaOH and 0.1M $Na_2CO_3$. The absorbance of the sample is read at 600 nm and the enzyme activity is determined from a standard curve prepared from a Thymol Blue standard. The standard curve is prepared by measuring absorbance of dilutions of a known standard and plotting the measured absorbance against the calculated enzyme activity in units per liter.

An end-point procedure may be employed for determination of acid phosphatase activity employing Thymol Blue Monophosphate as the substrate. In this instance, the test serum sample is added to a Thymol Blue Monophosphate solution buffered to a pH of about 5 and the reaction is terminated by addition of an alkaline reagent after 20 minutes reaction time. The absorbance of the sample is then read at 600 nm and the acid phosphatase enzyme activity is determined from a standard curve prepared from a Thymol Blue standard as described above.

The subject invention will now be illustrated with the following more detailed examples thereof. However, it is noted that the subject invention is not deemed as being limited thereto.

EXAMPLE I

Thymol Blue Monophosphate, Sodium Salt Solution

A mixture of 28 g Thymol Blue, 10 ml phosphorus oxychloride and 12 ml pyridine in 250 ml dry dioxane was allowed to react at room temperature for 2½ hours. The reaction mixture was poured into 500 ml water and agitated overnight. Thymol Blue Monophosphate was separated as an aqueous solution at pH 8.12 after extraction with 1:1 mixture of n-butanol/petroleum ether, ethylacetate and hexane. The total volume was one liter.

The concentration of Thymol Blue Monosphosphate, determined by exhaustive hydrolysis to Thymol Blue by alkaline phosphatase at pH 10, was 15 mmol/liter. The yield was approximately 25%. The solution, diluted 10 fold to approximately 1.5 mmol/liter, was used to prepare the working reagent for determination of alkaline phosphatase. The diluted solution of Thymol Blue Monophosphate was mixed 1:1 with 1.0M diethanolamine buffer at pH 10.2. The optical density (O.D.) of the freshly prepared working reagent at 600 nm was 0.042. A sample (2ml) of the working reagent was mixed with 50 µl of Validate A(control serum, General Diagnostics) and the rate of reaction at 30° C was observed in a spectrophotometer (Gilford 300-N) set at 600 nm. The rate was 0.0308/min. The enzyme activity was calculated to be 36 units per liter.

EXAMPLE II

Thymol Blue Monophosphate (AMPD Salt)

Five millimoles (2.33g) of Thymol Blue was dissolved in 100 ml dry tetrahydrofuran in a 250 ml 3-necked, roundbottomed flask equipped with a mechanical stirrer and a reflux condenser protected with a drying tube, and allowed to react with 1 ml (11 mM) phosphorus oxychloride and 1 ml (12 mM) pyridine. The resulting mixture was heated to reflux for one half hour then filtered. The filtrate was poured with stirring into a mixture of 120 ml 2 N hydrochloric acid and crushed ice. After several hours at room temperature the precipitate was removed by centrifugation. The precipitate was washed several times with 2 N hydrochloric acid and with water. The precipitate was then dissolved in sodium hydroxide solution at pH 10.6 and the alkaline solution was extracted with 1:1 mixture of n-butanol/petroleum ether, ethyl acetate and hexane. After extraction, the aqueous layer of volume 275 ml was at pH 7.7. The aqueous solution was adjusted to pH 4.0 with hydrochloric acid and extracted with ether. Salt was added to saturate the aqueous layer. Extraction with ether and with ethyl acetate caused separation of an orange-red solid at the interface of the solvents. The solid was collected on a frittered glass filter with suction and dissolved in ethanol. The solution of product, filtered to remove insoluble salts, was treated with alcoholic AMPD (2-amino-2-methyl-1, 3-propanediol). Addition of ether and chilling caused separation of a light orange precipitate which was collected on a porous filter with suction and the precipitate was washed with ether. Additional quantities of product were obtained by further dilutions of filtrate with ether. Thin layer chromatography (TLC) (silica gel, 95% ethanol) of the product showed a single yellow spot at $R_f$ 0.33, while the starting material (Thymol Blue) under the same conditions runs to $R_f$ 0.71 and turns blue upon exposure to ammonia. The NMR spectra were consistent with the structure of a monophosphate.

A solution of the product at pH 10.2 in a diethanolamine buffer containing magnesium chloride performed as a substrate for alkaline phosphatase as shown spectrophotometrically by the release of Thymol Blue on addition of sera containing alkaline phosphatase.

EXAMPLE III

Phosphorylated Thymol Blue

Fourteen grams (32 mM) Thymol Blue dried over phosphorous pentoxide in vacuum for two hours was suspended in 200 ml dry tetrahydrofuran in a 500 ml 3-necked, roundbottomed flask and allowed to react with 3 ml phosphorus oxychloride (33 mM) and 5 ml dry pyridine. The mixture was heated in reflux for one-half hour then poured into 2N HCl and cracked ice with stirring. The dark red gum formed was stirred several times with fresh volumes of 2N HCl and separated each time by centrifugation. The precipitate was dissolved in 2N NaOH and the solution (pH 6.0) was extracted with n-BuOH/Petroleum ether (1:1), ethyl acetate, and ether, and was then acidified to pH 2.5 and extracted twice with ethyl acetate. Addition of salt to the aqueous layer caused separation of a red, gummy solid which was taken up in methanol and dried over 3A molecular sieves (Linde) overnight. The methanolic solution was evaporated down, the residue was triturated with ethyl acetate and ether and the solid was collected on a glass filter with suction. After drying the solid, contaminated with inorganic salts, weighed 14.5 g. Trituration in ethyl acetate and ether produced a sample free of starting material. A solution of product (1 mg/50 ml) in pH 7.0 phosphate buffer showed a maximum absorption at a wavelength of 271 nm. The extinction coefficient $\epsilon$ of the Thymol Blue Monophosphate at 271nm was found to be 4, 963: at 405 nm $\epsilon = 7,910$. A sample of 2 mg of the solid in 2.9 ml diethanolamine buffer (ph 10.2) gave with 0.1 ml of control serum (Validate A) an absorbance rate (ΔA/min.) at 600 nm of 0.0180/min, while with a 5 mg sample the rate was 0.028/min.

EXAMPLE IV

Thymol Blue Monophosphate in Diethanolamine Buffer

Thirty millimoles (14g) Thymol Blue was suspended in approximately 200 ml dry tetrahydrofuran in 500 ml roundbottomed, three-necked flask equipped with a stirrer and a drying tube, and allowed to react for 2 hours at room temperature with 3 ml phosphorus oxychloride and 5 ml pyridine. The reaction mixture was filtered and the filtrate was concentrated under reduced pressure to 50-75 ml. The concentrate was poured into ice water and left standing overnight. The suspension at pH 1.5 centrifuged. The supernatants were combined, adjusted to pH 7.0, saturated with sodium sulfate, and extracted 3 times with ether. The aqueous layer after flashing off ether under reduced pressure was placed in a large evaporating dish and freeze-dried to give 66.5 g of an orange solid which appeared to contain inorganic salts. The orange solid was then suspended in absolute ethanol and after filtering off the salts, the solution was concentrated to 6.0g of an orange residue which was taken up in 1.OM DEA buffer (2.250 ml) at pH 10.2 to give a concentration of 2.6 mg/ml or 4.8 mmol/liter. A test volume of 2.9 ml showed an absorbance at 600 nm of 0.131 and a rate with 0.1 ml Lederzyme Control Sera (Lederle) at 30° C of 0.037/min. When refrigerated at 2° to 8° C over a period of 6 months, the buffered substrate showed an increase in absorbance at 600 nm to approximately 0.550 due to gradual hydrolysis, but the activity toward alkaline phosphatase remained unchanged. Frozen buffered substrate remained unchanged over the same storage period, i.e. its absorbance did not increase appreciably.

EXAMPLE V

Thymol Blue Monophosphate in a Freeze-Dried Formulation

Fourteen grams Thymol Blue was suspended in 250 ml dry tetrahydrofuran in 500 ml roundbottomed, 3-necked flask and allowed to react for 2-3 hours at room temperature with 3 ml phosphorus oxychloride and 4 ml pyridine. The mixture was filtered; the filtrate was poured into water and left in the cold overnight. The pH of the aqueous mixture was adjusted to pH 10 with aqueous potassium hydroxide, extracted twice with butanol, once with a mixture (1:1) of butanol petroleum ether, and twice with ether. Thin layer chromotography still showed a fast running impurity. The aqueous mixture was treated with sodium sulfate and extracted twice with butanol. TLC showed essentially one spot; no starting material and only slight amount of a fast running impurity. One more extraction of the aqueous solution with ether was followed by treatment with Celite and the Celite was removed by filtration. The pH of the solution was adjusted to 8 by addition of aq-hydrochloric acid. A mixture of 0.25 ml of this substrate and 2,65 ml 1M DEA buffer had an absorbance of 0.082 at 600 nm at 25° C. At the same temperature with 0.1 ml reference serum (Validate A control serum, General Diagnostics) the rate was measured at 0.0388/min.

A sample of the substrate solution was treated with solid AMPD at pH 11 and 0.2 ml aliquots were pipetted out into tubes for freezedrying. Freeze-dried reagent when reconstituted with 2.9 ml 1M DEA buffer had an absorbance at 600 nm of 0.288. The absorbance rate with 0.1 ml Validate A at 25° C was 0.0313/min. Tubes containing freeze-dried reagents were stored at room temperature for several months without appreciable changes in absorbance or activity.

EXAMPLE VI

Thymol Blue Monophosphate/Buffer Freeze-Dried Formulations

A. A solution of potassium Thymol Blue Monophosphate, pH 7.6 (0.3 ml and 2.6 ml 1M DEA buffer gave an optical density of 0.035 and an absorbance rate of 0.0312/min with 0.1 ml Validate A at 25° C) was treated with AMPD (5.25 g), sodium citrate (0.1 g), magnesium chloride hexahydrate (0.03 g), adjusted to pH 10.2 with hydrochloric acid and diluted with water to 50 ml in a volumetric flask. Aliquots of 1.2 ml were pipetted out into test tubes for freeze-drying. Freeze-dried samples, when reconstituted with 2.9 ml water had an absorbance at 600 nm of 0.143 and showed an absorbance rate of 0.0310/min with 0.1 ml Validate A at 25° C.

B. A solution of 200 mg of Thymol Blue Monophosphate Dicyclohexyl-ammonium salt in 50 ml 0.6M AMPD buffer was used for freeze-drying 1 ml aliquots in test tubes. Freeze-dried samples had a glassy appearance but were stable when stored at room temperature. Immediately after freeze-drying, the contents of a tube were reconstituted with 2.9 ml water and showed an absorbance at 600 nm of 0.202 and a rate with 0.1 ml Validate A of 0.0475/min. After one month at room temperature, 2.9 ml DEA buffer was added to each of two tubes and the absorbances at 600 nm were found to be 0.198and 0.194 respectively. After three months at room temperature, the absorbance was 0.195.

EXAMPLE VII

Freeze-Dried Formulations of Thymol Blue Monophosphate

A. An aqueous solution of Tris-buffered Thymol Blue Monophosphate, pH 8.9, was freeze-dried in aliquots of 0.3 ml to gummy orange residues. When reconstituted with 2 ml 0.6 M DEA buffer the solution had an optical density of 0.196 at 600 nm and gave a rate of 0.0584/min with 0.1 ml Validate A at 25° C.

B. Mannitol, 70 mg/ml, was added to an aqueous solution of Tris-buffered Thymol Blue Monophosphate, pH 8.9. Aliquots of 0.3 ml were freeze-dried to give an orange solid.

When reconstituted with 2 ml 0.6 M DEA buffer, the reagent had an optical density at 600 nm of 0.166 and gave an absorbance rate with 0.1 ml Validate A of 0.0552/min at 25° C. The pH was 10.19.

C. Magnesium oxide was added to an acidic solution of Thymol Blue Monophosphate to pH 9.7, then freeze-dried in 0.5 ml portions. Fluffy, orange plugs were obtained which when dissolved in 2 ml 0.6 M DEA buffer had an optical density of 0.154 at 600 nm and showed a rate of 0.0573/min at 25° C with 0.1 ml Validate A. The pH was 10.21.

D. A solution of Tris-buffered Thymol Blue Monophosphate was enriched with approximately 3% solid polyvinylpyrrolidine and freeze-dried in 0.3 ml aliquots to compact plugs. These were slow to dissolve in 2 ml 0.6 M DEA buffer 9pH 10.19). The optical density of the reagent at 600 nm was 0.087 and the rate of reaction with 0.1 ml Validate A at 25° C was 0.0582/min.

EXAMPLE VIII

Sodium Thymol Blue Monophosphate Solution

Thirty millimoles (14 g) Thymol Blue (Eastern Chemicals) was dispersed in 250 ml dry dioxane in a 500 ml, 3-necked, roundbottomed flask equipped with a stirrer and a drying tube, and allowed to react with 5 ml phosphorus oxychloride and 6 ml pyridine at room temperature for approximately 3 hours. The entire mixture was poured into 500 ml water. The pH was adjusted to 10 by additions of aq. 20% sodium hydroxide, and sodium chloride was added to saturate the aqueous phase which was extracted in succession with 2 volumes butanol/petroleum ether (1:1), one volume butanol/ethyl acetate (1:1), and one volume butanol. After extraction, the pH of the aqueous phase was 6.5. It was made alkaline again (pH 10) with sodium hydroxide and washed with ether to remove residual solvents.

On sitting at room temperature overnight, a voluminous orange precipitate separated from the saturated aqueous layer still at pH 10. The solids were collected by centrifugation and washed twice in centrifuge tubes with saturated sodium chloride solution. The yellow orange solid was readily soluble in water and slightly soluble in absolute ethanol. The material appeared to be essentially homogeneous by TLC ($SiO_2$; 95% EtOH) except for a trace of a higher $R_f$ contaminant.

The solids were dissolved in water, treated with a small amount of charcoal and Celite, then diluted to 4.5 liters with water and adjusted to pH 10. The concentration of substrate was determined by digesting with alkaline phosphatase at 30° C for 30 min to Thymol Blue and reading at 600 nm, to be approximately 2.5 mmol/liter. The overall yield amounted to 37.5% of the theoretical based on 30 mM of starting material.

When diluted with equal volume of 0.6 M DEA buffer (pH 10.2), (1 ml of the substrate solution and 1 ml buffer) the reagent had an optical density of 0.048 at 600 nm and showed a rate of 0.0758/min with 0.1 ml Validate A control serum (Lot 2685063, assayed to contain 31 units ALP by SMA 12/30 Technicon Standard).

EXAMPLE IX

Thymol Blue Monophosphate Dicyclohexylammonium Salt

Twenty-eight grams (60 mM) Thymol Blue in 250 ml dry tetrahydrofuran in 500 ml, 3-necked roundbottomed flask was allowed to react for two hours at room temperature with 6ml phosphorus oxychloride and 8 ml pyridine, then filtered. The filtrate was poured into 500 ml of water. Sodium hydroxide was added to achieve dissolution and the pH was adjusted to 10 prior to extracting three times with butanol/petroleum ether (1:1). TLC indicated impurities in the mixture. On sitting in the refrigerator overnight and after filtering the Celite, the filtrate was adjusted to pH 8.6, saturated with 200 g sodium sulfate and extracted several times with butanol/pet, ether (1:1), and once with butanol until TLC showed a very small amount of fast running impurity. The aq. mixture was acidified to pH 2.5 with 6 N hydrochloric acid and extracted with butanol (several portions). The organic extracts were combined, dried over Drierite, filtered, and allowed to react with 32.6 g(180 mM) dicyclohexylamine. After diluting with ether to a volume of approximately 2 liters, an orange precipitate separated which was collected on a filter with suction. The solid weighed 1.3 g. TLC showed essentially one spot ($R_f$ 0.5, ethanol and silica gel; methanol gave $R_f$ 0.75).

EXAMPLE X

Thymol Blue Monophosphate Cyclohexylammonium Salt

Thirty millimoles (14 g) Thymol Blue was suspended in 250 ml dry dioxane in 500 ml roundbottomed, 3-necked flask equipped with a mechanical stirrer and allowed to react with 3 ml phosphorus oxychloride and 4 ml dry pyridine. The reaction mixture was agitated under ambient conditions for two hours till the exotherm subsided, then filtered and the filtrate was poured into 500 ml water with stirring and the mixture was stirred for one to one and one-half hours. The pH was adjusted to 10 by adding 50% aq. potassium hydroxide. Sodium sultate (100 g) was added prior to extracting the mixture twice with butanol/ethyl acetate (1:1), twice with butanol/pet. ether (1:1), and twice with ether. (TLC showed presence of some Thymol Blue in the aqueous layer). Another 100 g portion of sodium sulfate was added to the aqueous layer and the pH was adjusted to 2.3 by adding aq. sulfuric acid. The saturated solution was extracted twice with ether and three times with butanol. The butanol extracts were combined, diluted with ether, dried over 3A molecular sieves, and allowed to react with an ethereal solution of 9 g (ca. 90 mM) cyclohexylamine. After standing at room temperature 1-2 hours, a precipitate formed in the flask and was collected by filtration and washed with ether. The orange solid after drying weighed 5.0 g and showed contamination with Thymol Blue on TLC.

The filtrate and the ether washed on sitting in the cold gave an orange precipitate that weighed 1.1 g. It contained no inorganic ash and almost no Thymol Blue. (After one month standing at room temperature, Thymol Blue was detected on TLC indicating decomposition). The orange compound changed color to brown in a transition on heating from ca. 265° C upward. A sample of 4 mg in 2.9 ml DEA buffer had an optical density at 600 nm of 0.061 and with 0.1 ml Validate A gave a rate of 0.0427/min at 25° C. The orange product was hygroscopic.

EXAMPLE XI

Thymol Blue Monophosphate Sodium Salt Solution

Fourteen grams (30 mM) Thymol Blue in 250 ml dry dioxane was allowed to react as previously described with 4.5 ml phosphorus oxychloride and 6 ml pyridine for 2 hours at ambient temperatures. The mixture was filtered and hydrolyzed in 500 ml water and adjusted to pH 8 by addition of sodium hydroxide. After saturating with sodium chloride, the mixture was extracted three times with butanol/pet. ether (1:1), the pH was adjusted to 2 and the product was extracted into several portions of butanol which were combined and washed with saturated salt solution prior to extraction into water (2 times) and 0.1N sodium hydroxide (2 times). The aqueous extracts were combined, adjusted to pH 10, washed with ether, evaporated till free of solvents on a rotoevaporator to 475 ml of a clear, dark red solution. A mixture of 0.2 ml red solution and 1.8 ml 1 M DEA buffer showed an optical density at 600 nm of 0.088 and gave with 0.1 ml Validate A reference serum at 25° C, a rate of 0.0577/min.

EXAMPLE XII

Thymol Blue Monophosphate Ammonium Salt

Fourteen grams (30 mM) Thymol Blue in 250 ml dry dioxane was reacted at room temperature with 4.5 ml phosphorus oxychloride in the presence of 6 ml pyridine. The work-up procedure was similar to that described above except that the butanol layer containing the reaction product was extracted with several portions of dilute aqueous ammonia (500 ml of 100 ml ammonia: 400 ml water). The alkaline extracts (pH 11.5) were washed with butanol (2 times) and with ether (3 times) and evaporated in a rotodryer, till effervescence ceased. TLC showed no Thymol Blue in the sample. A sample of the solution (0.2 ml with 1.8 ml 0.6 M DEA buffer) showed an optical density at 600 nm of 0.083 and gave a rate of 0.0486/min at 25° C with 0.1 Validate A.

EXAMPLE XIII

Thymol Blue Monophosphate, Tris (hydroxymethyl)aminomethane Salt

The reaction product from a treatment at room temperature of 14g Thymol Blue in 250 ml dry dioxane with 4.5 ml phosphorus oxychloride and 6 ml pyridine was hydrolyzed and worked up as described previously. The solution of product in butanol was dried over 3A molecular sieves and allowed to react with an excess of Tris base. The resulting salt was extracted into several portions of water. The combined aqueous layers (pH 8.8) were washed with butanol/ethyl acetate (1:1) and with ether prior to stripping under water suction to about 700 ml clear, amber liquid which showed potent substrate activity with alkaline phosphatase. A reagent of 0.3 ml substrate and 1.7 ml 0.6 M DEA buffer had an optical density of 600 nm of 0.059 and gave a rate with 0.1 ml Validate A of 0.0600/min (25° C).

Freeze-dried aliquots of 0.3 ml substrate in the presence of mannitol gave orange solid plugs that upon reconstitution with 2 ml 0.6 M DEA buffer had an optical density at 600 nm of 0.166, pH 10.19, and an absorbance rate of 0.0552/min at 25° C with 0.1 ml Validate A.

EXAMPLE XIV

Freeze-Dried Formulation of Thymol Blue Monophosphate Sodium Salt

Twenty milliliters of a solution of sodium salt of Thymol Blue Monophosphate was used to dissolve 1 g mannitol and 0.5 g AMPD (2-amino-2-methyl-1,3-propanediol). The pH was adjusted to 10.22 and the volume was brought to 25 ml with water. A test volume of 0.5 ml with 1.5 ml 0.6 M DEA buffer had an optical density at 600 nm of 0.042 and a rate of 0.0563/min with 0.1 ml Validate A at 25° C.

Aliquots of 0.5 ml were freeze-dried in small test tubes. The freeze-dried substrate was reconstituted with 2 ml 0.6 M DEA buffer. The optical density of 600 nm was 0.079 and the rate with 0.1 ml Validate A at 25° C was 0.0537/min (0.0718/min at 30° C).

EXAMPLE XV

Freeze-Dried Formulation of Thymol Blue Monophosphate Cyclohexylammonium Salt A stock solution for freeze-drying was made of 20 ml cyclohexylammonium salt of Thymol Blue Monophosphate, 1.5 g mannitol, and 0.5 g AMPD (2-amino-2-methyl-1,3-propanediol). The solution was adjusted to pH 10.29 and diluted to 25 ml. Aliquots of 0.8 ml were used for freeze-drying in small test tubes.

Freeze-dried substrate was reconstituted with 2 ml 0.6 M DEA buffer. The optical density at 600 nm was 0.054 and the rate with 0.1 ml Validate A at 30° C was found to be 0.0679/min. After one month at room temperature, a similarly reconstituted sample had an optical density at 600 nm of 0.075 and a rate of 0.0674/min with 0.1 ml Validate A at 30° C.

EXAMPLE XVI

Serum Alkaline Phosphatase - Kinetic Assay

A substrate for measurement of Alkaline Phosphatase by the kinetic method was prepared with the following composition: Thymol Blue Monophosphate 1.5 mmol/liter, diethanolamine buffer (pH 10.2) 0.5 mol/liter; magnesium chloride 1,5 mmol/liter. Two milliliters of the above was placed into a 1 cm cuvet in a spectrophatometer and brought to 30° C. To this was added 0.05 ml of the serum to be tested. The absorbance measured at 600 nm at one minute was 0.327, at five minutes was 0.437. From these two values, the change in absorbance ($\Delta A$/min) was, therefore, 0.022. The alkaline phosphatase enzyme level was calculated to be 26 units per liter.

EXAMPLE XVII

Serum Alkaline Phosphatase End Point Assay

A substrate for measurement of alkaline phosphatase by the end-point method prepared identical to that of example XVI. One ml of the reagent was placed in a suitable 10 ml tube for measurement of the test specimen and one ml of the reagent was placed in a second tube for measurement of the reagent blank. Both tubes were placed in a 37° C water bath for five minutes. The serum sample (0.1 ml) to be tested was added to the specimen tube and 0.1 ml of water to the blank tube. After 10 minutes incubation at 37° C, 3.0 ml of an alkaline solution that was 0.1 M in NaOH and 0.1 M in $Na_2CO_3$ was added to stop the reaction. The reagent blank solution was used to set the spectrophotometer at 0 absorption and the specimen tube was then measured and found to have an absorption of 0.329 at 600 nm. From a standard curve constructed from known concentrations of Thymol Blue an activity of alkaline phosphatase of 38 U/liter was determined.

EXAMPLE XVIII

Acid Phosphatase - End Point Assay

A reagent was prepared containing 1.2 mmol/liter of Thymol Blue Monophosphate, 0.05 M Citrate buffer pH 5.0, and 0.1 % non inonic detergent, Tergitol NPX (Union Carbide Corporation).

One ml of this substrate reagent solution was placed in each of two test tubes which were warmed to 37° C for 5 minutes. To one of the test tubes was added 0.2 ml of a serum sample containing an elevated level of acid phosphatase. The mixture was then permitted to stand at 37° C for 20 minutes at which time 3.0 mls of alkali reagent (0.1 m $Na_2CO_3$ + 0.1M NaOH) was added to stop the reaction. The second tube (blank) was incubated for 20 minutes at 37° C after which time 3.0 mls of the alkali reagent was added, immediately followed by 0.2 ml of the serum sample.

The absorption of each solution was measured at 600 nm against distilled water. The test serum sample had an absorption of 0.364. The blank had an absorption of 0.111 giving a net increase of 0.253 absorption units. From standard curve, the acid phosphatase activity of the serum was calculated to be 6.5 U/liter.

The embodiments of the invention in which an exclusive property or privilege is claimed are defined as follows:

1. Compounds useful in the assay of alkaline phosphatase enzymes comprising a compound having the structure

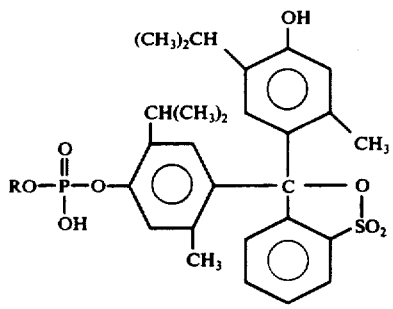

wherein R is selected from the group consisting of sodium, potassium, ammonium, 2-amino-2-methyl 1,3-propanediol, dicyclohexylamine, cyclohexylamine and tris(hydroxymethyl) amminomethane.

2. The compound of claim 1 wherein R is selected from the group consisting of sodium, potassium and ammonium.

3. A composition for the assay of alkaline phosphatase enzymes comprising a compound having the structure

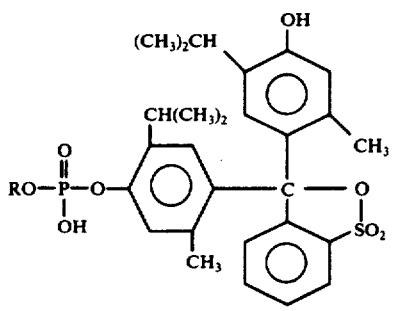

wherein R is selected from the group consisting of sodium, potassium, ammonium, 2-amino-2-methyl 1,3-propanediol, dicyclohexylamine, cyclohexylamine and tris(hydroxymethyl) aminomethane, a phosphorylatable buffer in an amount sufficient to produce a pH of about 10.2 and an activator for alkaline phosphatase in an amount sufficient to activate said alkaline phosphatase.

4. The composition of claim 3 wherein R is selected from the group sodium, potassium and ammonium.

5. The composition of claim 3 wherein said phosphorylatable buffer is diethanolamine.

6. The composition of claim 3 wherein said activator is an inorganic magnesium compound.

7. A method of assaying alkaline phosphatase enzymes present in a sample comprising contacting said sample with a composition which releases a dyestuff at a measurable rate, said composition comprising a compound having the structure

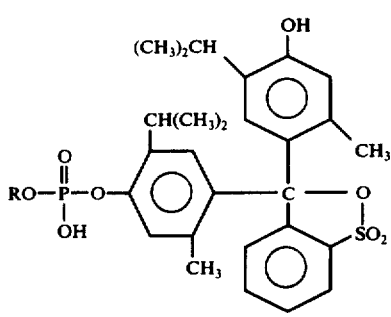

wherein R is selected from the group consisting of sodium, potassium, ammonium, 2-amino-2-methyl 1,3-propanediol, dicylohexylamine, cyclohexylamine and tris(hydroxymethyl) aminomethane, a phosphorylatable buffer in an amount sufficient to produce a pH of about 10.2 and an activator for alkaline phosphatase enzymes in an amount sufficient to activate said enzymes and spectrophotometrically measuring the rate of formation of dye.

8. A method of assaying alkaline phosphatase enzymes present in a sample comprising contacting said sample with a composition comprising a compound having the structure

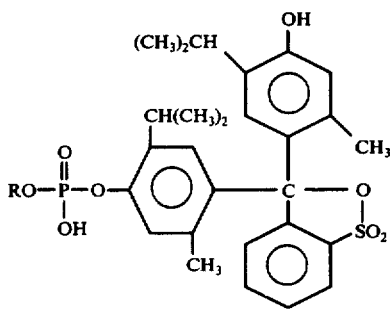

wherein R is selected from the group consisting of sodium, potassium, ammonium, 2-amino-2-methyl 1-3propanediol, dicyclohexylamine, cyclohexylamine and tris(hydroxymethyl) aminomethane, a phosphorylatable buffer in an amount sufficient to produce a pH of about 10.2 and an activator for alkaline phosphatase enzymes in an amount sufficient to activate said enzymes, adding alkali, and determining the absorbance of the resulting composition.

9. A method of assaying acid phosphatase enzyme present in a sample comprising contacting said sample with a composition comprising a compound having the structure

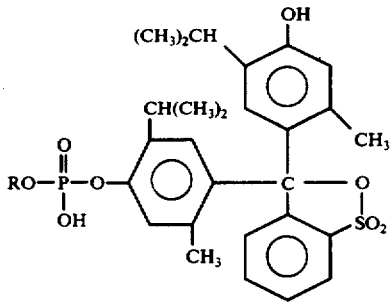

wherein R is selected from the group consisting of sodium, potassium, ammonium, 2-amino-2-methyl 1,3-propanediol, dicyclohexylamine, cyclohexylamine and tris (hydroxymethyl) aminomethane, a buffer in an amount sufficient to produce an acid pH, adding alkali and determining the absorbance of the resulting composition.

* * * * *